United States Patent
Mori et al.

(10) Patent No.: US 7,063,733 B2
(45) Date of Patent: Jun. 20, 2006

(54) FILTER MEMBER

(75) Inventors: Hisashi Mori, Yokohama (JP); Tadashi Kuwahara, Yokosuka (JP); Yasushi Nemoto, Fujisawa (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 10/481,055

(22) PCT Filed: Jun. 21, 2002

(86) PCT No.: PCT/JP02/06196

§ 371 (c)(1),
(2), (4) Date: Dec. 17, 2003

(87) PCT Pub. No.: WO03/000382

PCT Pub. Date: Jan. 3, 2003

(65) Prior Publication Data

US 2004/0163540 A1  Aug. 26, 2004

(30) Foreign Application Priority Data

Jun. 22, 2001 (JP) ............................. 2001-189833

(51) Int. Cl.
 *B01D 53/04* (2006.01)

(52) U.S. Cl. .......................... 96/135; 96/147; 96/153; 55/385.3; 55/486; 55/521

(58) Field of Classification Search .................. 96/55, 96/74, 134, 135, 147, 153, 154; 55/385.1, 55/486, 385.3, 497, 521, 523
See application file for complete search history.

(56) References Cited

U.S. PATENT DOCUMENTS

| | | | | | |
|---|---|---|---|---|---|
| 2,544,733 | A | * | 3/1951 | Shuler ........................ | 96/154 |
| 3,505,794 | A | * | 4/1970 | Nutter et al. ................. | 55/487 |
| 3,747,303 | A | * | 7/1973 | Jordan ........................ | 96/135 |
| 4,181,513 | A | * | 1/1980 | Fukuda et al. ................ | 96/153 |
| 4,259,096 | A | * | 3/1981 | Nakamura et al. ............ | 96/138 |
| 4,418,662 | A | * | 12/1983 | Engler et al. ................. | 96/133 |
| 4,906,263 | A | * | 3/1990 | von Blucher et al. ......... | 96/135 |
| 5,129,929 | A | * | 7/1992 | Linnersten .................. | 96/117.5 |
| 5,288,298 | A | * | 2/1994 | Aston ......................... | 96/135 |
| 5,328,758 | A | * | 7/1994 | Markell et al. .............. | 442/351 |
| 5,350,444 | A | * | 9/1994 | Gould et al. .................. | 96/154 |
| 5,354,365 | A | * | 10/1994 | Youn .......................... | 96/135 |
| 5,423,903 | A | * | 6/1995 | Schmitz et al. ............... | 96/134 |
| 5,486,410 | A | * | 1/1996 | Groeger et al. ............. | 442/353 |
| 5,605,746 | A | | 2/1997 | Groeger et al. | |
| 5,989,303 | A | * | 11/1999 | Hodge ........................ | 55/486 |

(Continued)

FOREIGN PATENT DOCUMENTS

DE  42 39 520  5/1994

(Continued)

OTHER PUBLICATIONS

EP Search Report for Application No. EP 02 74 3679 dated Sep. 29, 2004.

(Continued)

*Primary Examiner*—Robert H. Spitzer
(74) *Attorney, Agent, or Firm*—Sughrue Mion, PLLC

(57) ABSTRACT

A filter member which comprises one layer of deodorizing filter 1, which is composed of a reticulated filter substrate and a deodorizing agent adhering to the surface of its skeletons, and one or two layers of dust collecting filter 2a and 2b laminated on any one side or both sides thereof, with the resulting laminate being pleated.

21 Claims, 1 Drawing Sheet

U.S. PATENT DOCUMENTS

| | | | | |
|---|---|---|---|---|
| 6,090,184 | A * | 7/2000 | Cartellone | 95/69 |
| 6,197,079 | B1 * | 3/2001 | Mori et al. | 55/385.3 |
| 6,200,368 | B1 * | 3/2001 | Guerin et al. | 96/135 |
| 6,228,152 | B1 * | 5/2001 | Guerin et al. | 96/135 |
| 6,348,086 | B1 * | 2/2002 | Harms et al. | 96/125 |
| 6,375,699 | B1 * | 4/2002 | Beck | 55/497 |
| 6,454,834 | B1 * | 9/2002 | Livingstone et al. | 95/11 |
| 6,692,555 | B1 * | 2/2004 | Oda et al. | 96/134 |
| 2001/0035094 | A1 * | 11/2001 | Takagaki et al. | 96/154 |
| 2001/0052224 | A1 * | 12/2001 | Gelderland et al. | 55/521 |
| 2002/0043156 | A1 * | 4/2002 | Shea | 96/134 |
| 2002/0078828 | A1 * | 6/2002 | Kishkovich et al. | 96/108 |
| 2002/0088346 | A1 * | 7/2002 | Baracchi et al. | 96/134 |
| 2003/0089092 | A1 * | 5/2003 | Bause et al. | 55/524 |
| 2004/0050252 | A1 * | 3/2004 | Wernholm et al. | 95/143 |
| 2004/0055469 | A1 * | 3/2004 | Kroculick | 96/134 |

FOREIGN PATENT DOCUMENTS

| | | |
|---|---|---|
| DE | 198 34 311 | 2/2000 |
| EP | 0 803 275 | 10/1997 |
| EP | 0 955 087 | 11/1999 |
| EP | 1 323 459 | 7/2003 |
| JP | 56-047299 A | 4/1981 |
| JP | 57-014467 A | 1/1982 |
| JP | 61-046215 A | 3/1986 |
| JP | 04060320 A | 2/1992 |
| JP | 04074505 A | 3/1992 |
| JP | 04110532 A | 4/1992 |
| JP | 04-213335 A | 8/1992 |
| JP | 05-015485 A | 1/1993 |
| JP | 07-227510 A | 8/1995 |
| JP | 08-117524 A | 5/1996 |
| JP | 2000189734 A | 7/2000 |
| JP | 2000279505 A | 10/2000 |

OTHER PUBLICATIONS

Patent Abstracts of Japan, vol. 0172, No. 70 (C-1063), May 26, 1993 & JP 5 007725 A (Matsushita Electric Ind Co Ltd), Jan. 19, 1993 *abstract*.

Patent Abstracts of Japan, vol. 1999, No. 08, Jun. 30, 1999 & JP 11 060790 A (Mitsui Chem Inc), Mar. 5, 1999 *abstract*.

* cited by examiner

FILTER MEMBER

TECHNICAL FIELD

The present invention relates to a filter member which possesses a function of both deodorization and dust collection, and more particularly, to a filter member which excels in ability to eliminate odors and to collect fine dust while keeping its performance without appreciable pressure loss and clogging.

BACKGROUND ART

A variety of filters have found use in many fields. They include filters to remove trace gas from a clean room, filters for air cleaning, air conditioning, and ventilation, and filters that admit outside air into the automotive cabin (cabin filter). Filters are used also in fuel cells which are attracting attention recently. They are required to remove impurities from air (as an oxygen source) being supplied to the fuel cell. Thus, applications of filters are expanding more and more.

Under these circumstances, an ability to both collect dust and remove gaseous components is required of filters for air cleaners, air conditioners, ventilators, and automotive air ducts to admit outside air into the cabin.

Meanwhile, fuel cells are expected to be a promising technology to cope with global warming. For their operation, fuel cells need air as an oxygen source to be supplied to the oxygen electrode. Unfortunately, air contains sulfur compounds and organic compounds detrimental to the catalytic action in fuel cells. For stable output over a long period of time, fuel cells should be supplied with as pure air as possible after removal of impurities from outside air. This calls for filters with high deodorizing (gas removing) performance and high dust collecting performance. Moreover, filters for fuel cells should have low pressure loss as well as high deodorizing and dust collecting performance because auxiliary equipment (such as blowers) should run with low energy consumption for improved energy conversion efficiency.

It has been common practice to collect comparatively fine dust smaller than 10 μm (referred to as fine dust hereinafter) by using filters made of polypropylene fiber, polyester fiber, polyamide fiber, glass fiber, or the like. Such filters are nonwoven fabrics produced from polymers by spun bonding or melt blowing. There is known a charged filter which is highly capable of collecting fine dust by Coulomb force due to charge on an easily chargeable non-polar polymer such as polypropylene, as disclosed in Japanese Patent Publication Nos. Sho 56-47299, Sho 57-14467, and Hei 5-15485, and Japanese Patent Laid-open Nos. Sho 61-46215, Hei 4-213335, and Hei 7-227510.

There are other filters such as net-like ones formed from polypropylene or polyethylene resin and those of three-dimensionally reticulated polyurethane foam, which are used for collection of comparatively coarse dust larger than 10 μm (referred to as coarse dust hereinafter).

Unfortunately, the former fibrous filters are liable to clogging, which decreases efficiency soon, despite their good ability to collect fine dust, and the latter net-like filters lack an ability to collect fine dust.

There has been proposed a filter to achieve dust removal and deodorization simultaneously which is formed into a desired shape from a deodorizing agent and a dust removing material by using a binder (Japanese Patent Laid-open No. Hei 8-117524). This filter, however, is not necessarily good in deodorizing performance because it merely permits a limited amount of deodorizing agent to be incorporated thereinto so that it keeps its low initial pressure loss. Another filter for simultaneous deodorization and dust removal is one which is a simple laminate composed of a deodorizing layer and a dust collecting layer. It has the disadvantage of being poor in deodorizing and dust removing performance per unit amount of pressure loss.

There has been proposed another type of filter which is composed of two layers of nonwoven fabrics (both capable of dust collection) laminated on top of the other, with deodorizing particles attached to the inside of one layer by means of a hot-melt adhesive. Unfortunately, this filter is inherently liable to clogging if it is intended mainly to collect fine dust, and this prevents incorporation with a sufficient amount of deodorizing agent. Conversely, the filter will be very poor in ability to collect fine dust if it is sufficiently incorporated with a deodorizing agent.

As explained above, conventional filters cannot exhibit both dust collecting ability and deodorizing ability when they are used in areas, such as ventilation, air conditioning, automobiles, and fuel cells, where an increase in initial pressure loss after filter mounting or an increase in pressure loss due to clogging with dust is not permissible because it lowers the blowing capacity. They do not meet all the requirements.

There has been proposed a pleated filter member which is expected to have both dust collecting ability and deodorizing ability. It is made of polyurethane foam with three-dimensionally reticulated skeletons free of cell membrane, and it is used as the base of deodorizing filters or dust collecting filters. Although it collects coarse dust efficiently without becoming clogged easily and it is also capable of deodorization, it is limited in the amount of deodorizing agent to be incorporated thereinto because it increases in initial pressure loss if it is designed for efficient collection of fine dust.

DISCLOSURE OF THE INVENTION

It is an object of the present invention, which was completed in view of the foregoing, to provide a high-performance filter member which is capable of collecting both coarse dust and fine dust, permits incorporation with a sufficient amount of deodorizing agent for deodorization to a desired extent, and achieves dust collection and deodorization in a well-balanced manner at a low pressure loss without becoming clogged easily.

After their extensive studies carried out to achieve the above-mentioned object, the present inventors found that a high-performance filter member can be obtained if one layer of deodorizing filter, which is composed of a reticulated filter substrate and a deodorizing agent adhering to the surface of its skeletons, is laminated with one or two layers of dust collecting filter, and the resulting laminate is entirely pleated. The resulting filter member accomplishes collection of both fine and coarse dust and deodorization equally well at a low pressure loss without clogging. Such performance has never been attained by the conventional technology. The present invention was completed on the basis of this finding.

Thus, the present invention is directed to a filter member which includes one layer of deodorizing filter, which is composed of a reticulated filter substrate and a deodorizing agent adhering to the surface of its skeletons, and one or two layers of dust collecting filter laminated on any one side or both sides thereof, with the resulting laminate being pleated.

Incidentally, the term "deodorization" used in this specification implies removal of any gaseous components as well as removal of odor components.

BEST MODE FOR CARRYING OUT THE INVENTION

Figure 1:
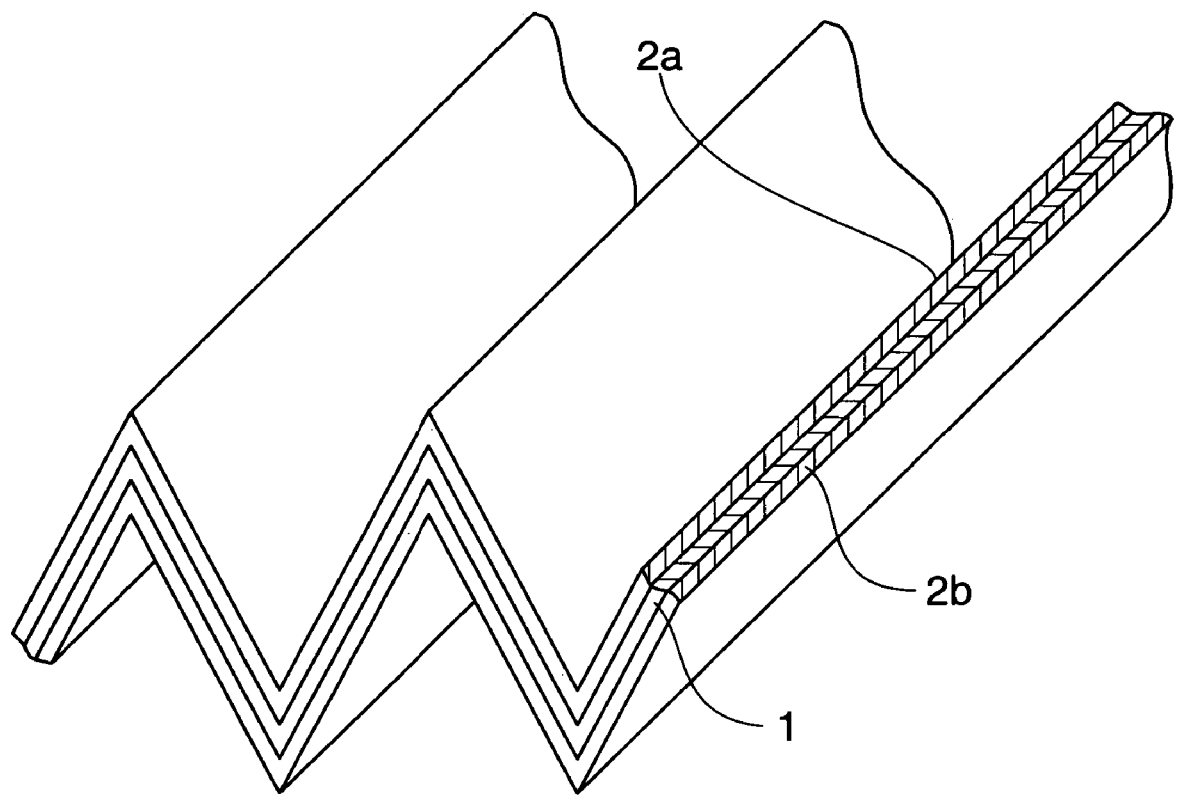
FIG. 1 is a partly enlarged perspective view showing a filter member pertaining to one embodiment of the present invention.

A detailed description of the present invention will be given below.

As shown in FIG. 1, the filter member according to the present invention is typically composed of a deodorizing filter layer 1 and one or two dust collecting filter layers 2a and 2b laminated on any one side or both sides thereof (the latter case is shown in FIG. 1), with the resulting laminate being pleated.

The layer of deodorizing filter 1 is prepared from a reticulated filter substrate and a deodorizing agent adhering to the surface of the skeletons thereof. The reticulated filter substrate is highly breathable, permits a large amount of deodorizing agent to adhere thereto, and retains sufficient strength after pleating.

The reticulated filter substrate for the deodorizing filter 1 may be made of polypropylene, polyethylene, polyester, polyamide, or the like, without specific restrictions. The reticulated filter substrate is composed of strands usually forming squares, rectangles, hexagons, rhombuses, or the like without specific restrictions. Strands may form two or more of these figures in combination. The spacing and thickness of strands should be properly established in consideration of the initial pressure loss desired, the particle size of the deodorizing agent, and the strength of the pleats, although they are not specifically restricted. Preferably, spacing of strands is usually 1 to 15 mm, particularly 2 to 6 mm, so that the reticulated filter substrate has a low pressure loss and a high capacity for incorporation with deodorizing agent and retains its strength after pleating. Adequate thickness of strands is usually 0.1 to 2 mm, particularly 0.3 to 1 mm, so that the reticulated filter substrate keeps its low pressure loss and retains its strength at the sharp ridges of pleats.

The reticulated filter substrate may be primed so that the strand surface is coated easily with a binder (mentioned later). Priming includes dipping in a resin solution (such as epoxy and polyacrylic acid) and corona discharge treatment which physically roughens the strand surface. The reticulated filter substrate should preferably undergo preliminary biaxial orientation so that it will not deform due to tension and heat during binder coating mentioned later and pleating.

The deodorizing agent to be applied to the reticulated filter substrate may be selected properly without specific restrictions according to the intended purpose. Its typical examples include petroleum pitch-based activated carbon, coconutshell-based activated carbon, pellet-formed activated carbon, wood-based activated carbon, natural or synthetic zeolite, $SiO_2$, ZnO, $TiO_2$, silica gel, activated clay, cation or anion exchange resin, manganese oxide, and alumina. They may be used alone or in combination with one another. In addition, the deodorizing agent should preferably be in spherical or spheroidal shape with a low fluid resistance because it greatly affects the pressure loss of the resulting filter member.

The deodorizing agent (adsorbent) variously affects the performance of fine dust collection depending on its type selected. The one which gives off little dust is desirable. Its typical examples include petroleum pitch-based or coconut-shell-based activated carbon and zeolite whose spherical particles are coated with a porous polymeric layer of polyester, polytetrafluoroethylene (PTFE), polypropylene, or the like.

Of the above-mentioned deodorizing agents, activated carbons with a large specific surface area for adsorption are desirable from the standpoint of deodorizing performance; however, they are disadvantageous for removal of gaseous components with a low molecular weight and a strong polarity because they depend mainly on van der Waals force for their adsorption. They should preferably be incorporated with an adequate additive for improvement in deodorizing performance.

The additive includes chemicals which neutralize acids or bases, or condense aldehyde and amine by Schiff reaction. The former is exemplified by phosphoric acid, hydrochloric acid, malic acid, etc. (as acidic additives) and sodium carbonate, sodium metasilicate, KOH, NaOH, etc. (as basic additives). The latter is exemplified by aminophenylacetic acid, aminobenzoic acid, aminobenzenesulfonic acid, etc.

The deodorizing filter layer 1 as a constituent of the filter member of the present invention is composed of the reticulated filter substrate and the deodorizing agent attached to the skeletons thereof. There are no specific restrictions as to the method of attaching particles of deodorizing agent to the reticulated filter substrate. This object is achieved usually by forming a binder layer on the surface of the skeletons of the reticulated filter substrate and then attaching the particulate deodorizing agent to the binder layer. Desirable examples of the binder include polyamide, polyolefin, ethylene-vinyl acetate copolymer, synthetic rubber, polyurethane, and acrylic resin in the form of hot melt or non-solvent emulsion.

The layers of dust collecting filter 2a and 2b which are laminated onto the layer of deodorizing filter mentioned above are not specifically restricted so long as they are capable of collecting dust. Desirable ones include a fibrous filter or a polyurethane foam free of cell membrane.

The fibrous material may be formed from any material, such as polypropylene, polyethylene, polyester, and glass, which are not specifically restricted. They may be used alone or in combination with one another. For desired effects, their fiber diameter should preferably be 1 to 100 µm, particularly 10 to 50 µm, and their basis weight should be 20 to 200 g/m², particularly 35 to 75 g/m². An excessively large fiber diameter is disadvantageous for the ability to mechanically collect dust, and conversely an excessively small fiber diameter promotes clogging. An excessively large basis weight increases pressure loss, and conversely an excessively small basis weight is detrimental to the dust collecting performance.

The fibrous filter mentioned above may be prepared in the form of melt-blow nonwoven fabric, spun-bond nonwoven fabric, glass fiber nonwoven fabric, or their composite nonwoven fabric from the above-mentioned fibers. Nonwoven fabrics with needle punching are preferable.

The three-dimensionally reticulated polyurethane foam (free of cell membrane) as the dust collecting filter should preferably be a polyether-based or polyester-based polyurethane foam. Its typical example includes "Everlight SF" commercially available from Bridgestone Kaseihin Seizo Co., Ltd.

Incidentally, the fibrous filter or the dust collecting filter layers 2a and 2b of polyurethane foam should preferably be given antistatic treatment, although not mandatory.

There are no specific restrictions as to the method of laminating the dust collecting filter layers 2a and 2b onto the deodorizing filter layer 1. Lamination may be accomplished by using an adhesive, such as polyamide, polyolefin, ethylene-vinyl acetate copolymer, synthetic rubber, polyurethane, and acrylic resin in the form of hot melt or non-solvent emulsion. Bonding with a hot melt in the form of nonwoven fabric or a hot melt spread like a spider's web is desirable from the standpoint of keeping pressure loss low and preventing the gas adsorbing performance from deterioration.

Good bonding with an adhesive can be achieved between the deodorizing filter layer 1 and the dust collecting filter layers 2a and 2b if the reticulated filter substrate as a constituent of the deodorizing filter layer 1 is previously given priming treatment such as corona discharge and resin coating as mentioned above. This priming treatment improves affinity for the adhesive, thereby ensuring firm adhesion.

The filter member of the present invention includes one layer of deodorizing filter and one or two layers of dust collecting filter laminated onto any one side or both sides of the layer of deodorizing filter. A filter member of three-layer structure as shown in FIG. 1 is desirable although it is not mandatory. It includes one layer of deodorizing filter 1 and two layers of dust collecting filter 2a and 2b laminated onto both sides thereof. In this case, it is desirable to place a coarse dust collecting filter 2a on the obverse side (into which the raw gas flows) and to place a fine dust collecting filter 2b on the reverse side (from which the filtrate leaves). This arrangement is appropriate from the standpoint of avoiding clogging.

In other words, a desirable way to effectively protect the filter from clogging in principle is to permit the filter to catch dust particles varying in size sequentially in the order of decreasing particle size. This object is achieved lo if the dust collecting filter has a density gradient. According to the present invention, a desirable density gradient can be readily established by laminating the layer of deodorizing filter 1 with the coarse dust collecting filter 2a on its upstream side and with the fine dust collecting filter 2b on its downstream side.

This object is achieved if the coarse dust collecting filter 2a is formed from the three-dimensionally reticulated polyurethane foam free of cell membrane (mentioned above) and the fine dust collecting filter 2b is formed from the fibrous filter (mentioned above), particularly polypropylene-based electret nonwoven fabric which excels in fine dust collecting performance. Any other construction may also be possible.

Incidentally, the filter member of the present invention takes on a pleated form, and pleating can be accomplished in the usual way by using any known pleating machine.

In what follows, the present invention will be described in more detail with reference to Examples and Comparative Examples which are not intended to restrict the scope of the invention.

EXAMPLE

Example 1

A reticulated filter substrate, 300 mm wide and 2000 mm long, was cut out of plastic netting "Nisseki Conwed-net" (from Nisseki Sheet Pallet System Co., Ltd.) as specified below.

Basis weight: 49 g/m$^2$

Average spacing of strands: 4 mm in both longitudinal and lateral directions

Average net thickness: about 0.7 mm in the vicinity of the nodal point of longitudinal and lateral strands Average strand thickness: about 0.3 mm (both longitudinal and lateral strands)

The above-mentioned reticulated filter substrate was dipped in a binder of acrylic-based emulsion ("EW-2500" from Soken Chemical & Engineering Co., Ltd.), with pickup being 30 g/m$^2$ (on dry basis). Dipping was followed by complete drying at 80° C., so that a binder layer was formed on the surface of strands. To the binder layer were attached (with the aid of its tackiness) spherical particles of petroleum pitch-based activated carbon ("G-70R" from Kureha Chemical Industry Co., Ltd.). Thus there was obtained a flat reticulated deodorizing filter layer which carries 500 g of activated carbon per square meter.

Then, to each side of the deodorizing filter layer was laminated a dust-collecting filter layer, with an interlayer placed between them. Lamination was accomplished by hot pressing at 130° C. for 20 seconds. The interlayer is a polyamide-based hot melt nonwoven fabric cut in the same size as above ("PA-150" from Diabond Industry Co., Ltd.). The dust-collecting filter layer, which is placed on the obverse side (or upstream side) of the deodorizing filter, is for coarse dust collection, and it is a three-dimensionally reticulated polyether-based polyurethane foam free of cell membrane ("Everlight SF FQ-40$^{1″}$" from Bridgestone Corp.), measuring 1 mm thick, 300 mm wide, and 2000 mm long. The dust-collecting filter layer, which is placed on the reverse side (downstream side) of the deodorizing filter, is for fine dust collection, and it is a polypropylene-based electret nonwoven fabric ("SB050N" from Toray Fine Chemicals Co., Ltd.). Thus there was obtained a filter sheet of three-layer structure.

The filter sheet was pleated (30 mm high) by using a pleating machine of reciprocating type. The pleats were fixed at a pitch of 12 mm with a polyester nonwoven fabric, 1.5 mm thick, having a basis weight of 100 g/m$^2$ and a 50 μm thick coating of polyolefin hot melt. Thus there was obtained a pleated filter member which carries about 2500 g of activated carbon per square meter of projected area.

Example 2

The same procedure as in Example 1 was repeated to give a flat deodorizing filter layer, which carries 550 g of activated carbon per square meter, except that the reticulated filter substrate was replaced by a plastic netting "Nisseki Conwed-net ON6200" (from Nisseki Sheet Pallet System Co., Ltd.) as specified below.

Basis weight: 34 g/m$^2$

Average spacing of strands: 3.5 mm in longitudinal direction and 4 mm in lateral direction Average net thickness: about 0.45 mm in the vicinity of the nodal point of longitudinal and lateral strands Average strand thickness: about 0.3 mm (longitudinal strands) and 0.15 mm (lateral strands)

Then, to both sides of the deodorizing filter layer were laminated dust-collecting filter layers (one for coarse dust collection and one for fine dust collection) in the same manner as in Example 1.The resulting laminate was pleated. Thus there was obtained a pleated filter member which carries about 2750 g of activated carbon per square meter of projected area.

The filter members obtained in Examples 1 and 2 were tested for breathability, fine dust collecting performance, life to clogging, and coarse dust collecting performance in the following manner by using a vertical wind tunnel (250 by 250 mm inside) specified by the Japan Air Cleaning Association. For comparison, the same test as above was performed on a cabin filter which is composed of two layers of polypropylene nonwoven fabrics bonded together with an adhesive, with crashed activated carbon held between them. The results of tests are shown in Table 1.

Details of filter member for comparison are as follows.

Details of Filter Member for Comparison
    Shape: pleated (height: 29 mm, pitch: 6.5 mm, expansion ratio: approx. 9)
    Amount of activated carbon: about 300 g/m² (flat area), and about 2700 g/m² (projected area)

[Test Methods]

Breathability
    Expressed in terms of initial pressure loss (in Pa) at a wind velocity of 3.5 m/s.

Fine Dust Collecting Performance
    Expressed in terms of the ratio of airborne dust (0.3 to 0.5 μm) collected at a wind velocity of 1.5 m/s.

Life to Clogging
    Expressed in terms of the amount of dust collected per unit area of the sample filter member until the initial pressure loss increases by 150 Pa when the sample filter member collects dust (15 kinds specified in JIS) continuously at a rate of 0.6 g/min from air flowing at a wind velocity of 3.5 m/s.

Coarse Dust Collecting Performance
    Expressed in terms of the ratio (%) of dust retained per unit area of the sample filter member until the initial pressure loss increases by 150 Pa when the sample filter member collects dust (15 kinds specified in JIS) continuously at a rate of 0.6 g/min from air flowing at a wind velocity of 3.5 m/s.

TABLE 1

| | Example 1 | Example 2 | Comparative Example |
|---|---|---|---|
| Amount of activated carbon in flat area (g/m²) | 500 | 550 | 300 |
| Expansion ratio of pleats | ×5 | ×5 | ×9 |
| Amount of activated carbon in projected area (g/m²) | 2500 | 2750 | 2700 |
| Initial pressure loss at a wind velocity of 3.5 m/min (Pa) | 103 | 101 | 115 |
| Fine dust collecting performance in terms of ratio of collection of airborne dust, 0.3 to 0.5 μm, (%) | 23.5% | 23.00% | 3.50% |
| Life to clogging in terms of amount of dust collected for initial pressure loss to increase by 150 Pa (g/m²) | 368 | 357 | 302 |
| Coarse dust collecting performance in terms of ratio of retained dust (%) | 94.50% | 93% | 90% |

It is noted from Table 1 that the filter member according to the present invention produces the following effects (1) to (4) in contrast to the conventional one.
    (1) Lower pressure loss for the same amount of deodorizing agent.
    (2) Better fine dust collecting performance (about 6.5 times or above) for the same amount of deodorizing agent.
    (3) Equal or better coarse dust collecting performance for the same amount of deodorizing agent.
    (4) Well-balanced effective improvement in fine dust collecting performance, deodorizing performance, and clogging prevention without appreciable increase in pressure loss.

As mentioned above, the filter member according to the present invention can collect both coarse dust and fine dust and adsorb odor with a sufficient amount of deodorizing agent in a well-balanced manner with little liability to clogging at a reasonably low pressure loss.

The invention claimed is:

1. A filter member:
comprising one layer of deodorizing filter, which is composed of a reticulated filter substrate having a skeleton comprising strands and a deodorizing agent adhered to a surface of the skeleton, and at least one layer of dust collecting filter laminated on at least one side thereof, with the resulting laminate being pleated,
wherein said reticulated filter substrate is formed from one of polypropylene, polyethylene, polyester, and polyamide and said deodorizing agent used for said layer of deodorizing filter comprises spherical or spheroidal particles formed of at least one of petroleum pitch-based activated carbon, coconutshell-based activated carbon, pellet-formed activated carbon, wood-based activated carbon, natural or synthetic zeolite, $SiO_2$, $ZnO$, $TiO_2$, silica gel, activated clay, cation or anion exchange resin, manganese oxide, and alumina.

2. A filter member as defined in claim 1, wherein said layer of deodorizing filter and said layer of dust collecting filter are bonded together with an adhesive.

3. A filter member as defined in claim 2, wherein said adhesive is selected from a group of polyamide, polyolefin, ethylene-vinyl acetate copolymer, synthetic rubber, polyurethane, and acrylic resin in the form of hot melt or non-solvent emulsion.

4. A filter member as defined in claim 2, wherein said adhesive is a hot melt in the form of nonwoven fabric or a hot melt spread like a spider's web.

5. A filter member as defined in claim 2, wherein said reticulated filter substrate as a constituent of said layer of deodorizing filter is primed by corona discharge treatment or resin coating to improve affinity for said adhesive.

6. A filter member as defined in claim 1, wherein said reticulated filter substrate as a constituent of said layer of deodorizing filter has undergone biaxial orientation.

7. A filter member as defined in claim 1, wherein said strands have a spacing of 1 to 15 mm and a thickness of 0.1 to 2 mm.

8. A filter member as defined in claim 1, wherein said strands form one or more shapes of squares, rectangles, hexagons, and rhombuses.

9. A filter member as defined in claim 1, wherein said deodorizing agent is one which is incorporated with a chemical which reacts with aldehydes through Schiff reaction.

10. A filter member as defined in claim 1, wherein said deodorizing agent is one which is incorporated with a chemical which neutralizes an acid or base.

11. A filter member as defined in claim 1, wherein said surface of said skeleton comprises a binder layer and said deodorizing agent adheres to said binder layer.

12. A filter member as defined in claim 11, wherein said binder layer is selected from a group of polyamide, polyolefin, ethylene-vinyl acetate copolymer, synthetic rubber, polyurethane, and acrylic resin in the form of hot melt or non-solvent emulsion.

13. A filter member as defined in claim 1, wherein said layer of dust-collecting filter is formed from a fibrous filter.

14. A filter member as defined in claim 13, wherein said fibrous filter is composed of one or more kinds of fibers selected from a group of polypropylene fiber, polyethylene fiber, polyester fiber, and glass fiber, and these fibers have a fiber diameter of 1 to 100 µm.

15. A filter member as defined in claim 13, wherein said fibrous filter is a fabric having a basis weight of 20 to 200 g/m$^2$.

16. A filter member as defined in claim 13, wherein said fibrous filter is one or more kinds of composite nonwoven fabrics selected from a group of melt blow nonwoven fabric, spun bond nonwoven fabric, and glass fiber nonwoven fabric, and the nonwoven fabric has undergone needle punching.

17. A filter member as defined in claim 1, wherein said layer of dust-collecting filter is a three-dimensionally reticulated polyether-based or polyester-based polyurethane foam free of cell membrane.

18. A filter member as defined in claim 1, wherein said layer of dust-collecting filter has undergone antistatic treatment.

19. A filter member as defined in claim 1, wherein said layer of deodorizing filter is laminated with a layer of filter to collect coarse dust on the obverse side thereof and with a layer of filter to collect fine dust on the reverse side thereof, and raw gas enters the filter layer on the obverse side and leaves from the filter layer on the reverse side, thereby removing dust and gaseous components.

20. A filter member as defined in claim 19, wherein said layer of filter to collect coarse dust is formed from a three-dimensionally reticulated polyether-based or polyester-based polyurethane foam free of cell membrane, and said layer of filter to collect fine dust is formed from a fibrous filter.

21. A filter member:

comprising one layer of deodorizing filter, which is composed of a reticulated filter substrate having a skeleton and a deodorizing agent adhered to a surface of the skeleton, and at least one layer of dust collecting filter laminated on at least one side thereof, with the resulting laminate being pleated, wherein said deodorizing agent used for said layer of deodorizing filter comprises spherical or spheroidal particles formed of at least one of petroleum pitch-based activated carbon, coconutshell-based activated carbon, pellet-formed activated carbon, wood-based activated carbon, natural or synthetic zeolite, $SiO_2$, ZnO, $TiO_2$, silica gel, activated clay, cation or anion exchange resin, manganese oxide, and alumina, wherein said layer of deodorizing filter and said layer of dust collecting filter are bonded together with an adhesive, and wherein said reticulated filter substrate as a constituent of said layer of deodorizing filter is primed by corona discharge treatment or resin coating to improve affinity for said adhesive.

* * * * *